(12) United States Patent
Krzypow et al.

(10) Patent No.: US 7,979,110 B1
(45) Date of Patent: Jul. 12, 2011

(54) METHOD FOR ACCURATE PLACEMENT OF ELECTRODES

(75) Inventors: David Krzypow, University Heights, OH (US); Brian M. Kolkowski, Leroy, OH (US)

(73) Assignee: Orbital Research Inc., Cleveland, OH (US)

( * ) Notice: Subject to any disclaimer, the term of this patent is extended or adjusted under 35 U.S.C. 154(b) by 1195 days.

(21) Appl. No.: 10/947,719

(22) Filed: Sep. 23, 2004

(51) Int. Cl.
*A61B 5/0402* (2006.01)
(52) U.S. Cl. ........................................ 600/509; 606/186
(58) Field of Classification Search .......... 606/185–186; 600/508–509, 372, 300; 607/1–2, 115
See application file for complete search history.

(56) References Cited

U.S. PATENT DOCUMENTS

| | | | | |
|---|---|---|---|---|
| 2,588,623 A * | 3/1952 | Eliscu et. al. | ................... | 604/47 |
| 4,576,170 A * | 3/1986 | Bradley et al. | ................... | 607/27 |
| 5,293,867 A | 3/1994 | Oommen | | |
| 5,496,304 A * | 3/1996 | Chasan | ............... | 606/1 |
| 5,916,157 A * | 6/1999 | Crosz, Jr. | ..................... | 600/372 |
| 6,013,122 A * | 1/2000 | Klitzman et al. | ........... | 106/31.03 |
| 6,355,649 B1 * | 3/2002 | Gormley et al. | .............. | 514/284 |
| 6,400,975 B1 * | 6/2002 | McFee | ............. | 600/372 |
| 6,689,095 B1 * | 2/2004 | Garitano et al. | ................ | 604/70 |
| 7,337,007 B2 * | 2/2008 | Nathan et al. | ................... | 607/48 |
| 7,444,177 B2 * | 10/2008 | Nazeri | ............. | 600/382 |
| 2002/0123694 A1 * | 9/2002 | Organ et al. | ................. | 600/547 |
| 2003/0100603 A1 * | 5/2003 | Beinlich et al. | ............... | 514/458 |
| 2004/0158196 A1 * | 8/2004 | Garitano et al. | ................ | 604/68 |

OTHER PUBLICATIONS

Meriam-Webster, Inc., Webster's Ninth New Collegiate Dictionary, pp. 104, 401 and 728.*

* cited by examiner

*Primary Examiner* — Carl H Layno
*Assistant Examiner* — Frances P Oropeza
(74) *Attorney, Agent, or Firm* — Brian M. Kolkowski; Matthew Beutler

(57) ABSTRACT

The currently claimed invention is for a method of placement of certain medical devices, and in particular, to the placement of electrodes in the field biopotential or electrophysiological monitoring. More particularly, it provides a new method for marking the skin of a subject where medical electrodes are to be placed including the placement of an electrode harness containing these electrodes. The method for accurate placement of electrodes of the currently claimed invention provides a quick, efficient method of electrode placement and replacement. This method further allows homecare providers or even the patient themself to accurately place and replace electrodes for home health care or outpatient monitoring.

20 Claims, 3 Drawing Sheets

METHOD FOR ACCURATE PLACEMENT OF ELECTRODES

BACKGROUND OF THE INVENTION

1. Field of the Invention

The present invention relates to a method for placement of certain medical devices. In particular, it pertains to the placement of electrodes in the field biopotential or electrophysiological monitoring. More particularly, it provides a new method for marking the skin of a subject where medical electrodes are to be placed including the placement of an electrode harness containing these electrodes.

2. Technical Background

Electrodes are used in the medical field for monitoring biopotential of different subjects including patients. Groups of two or more electrodes are commonly used in order to allow for a variety of types of analysis. Such types of analysis include ECG (or EKG), EEG, EMG, and other such biopotential measurements using standard sensors such as electrodes. Many standard EKG measurements such as the commonly performed "stress test" require up to 12 separate electrodes to be placed on the skin of the subject in precise correlation to the patient's anatomical features. For many biopotential measurements, specific anatomical placement of electrodes is required for accurate measurements. In some instances, misplacement of electrodes by as much as a half an inch could lead to faulty measurements and misdiagnosis. Such accurate placement has in the past, and continues to require a highly trained medical specialist such as a doctor or nurse. Availability of one of the aforementioned medical specialists is generally not an issue in an inpatient setting. However, increasing use of "at home" or ambulatory monitoring presents the problem of placing the patient in a monitoring setting where no healthcare professional is available to properly place electrodes.

Generally, an at home monitoring setup is conducted at the hospital where electrodes and accompanying wires or harness are accurately placed on the patient by a healthcare professional. The patient is instructed to wear the electrodes and harness 24 hours a day for in some cases a number of days without removal to ensure that the proper placement of the electrodes is maintained. The patient is also instructed not to bathe during this time period. Periodically, the patient may return for placement of new electrodes.

There is currently a need in the healthcare field for a way to enable ambulatory monitoring of patients that allows for patients or their untrained healthcare providers to properly place monitoring electrodes. There are many factors contributing to this need for ambulatory monitoring. The greatest factor is the high cost of healthcare and especially inpatient care. Hospital stays routinely cost a thousand dollars a day, with intensive care unit (ICU) and cardiac care unit stays greatly elevating this cost. Many healthcare providers and insurance companies consider it a waste of valuable resources and scarce hospital beds to keep an otherwise stable patient in a hospital when their only requirement is medial monitoring.

In the past, the problem with ambulatory monitoring has been its decreased accuracy due to patient compliance with monitoring procedures. Monitored patients routinely violate their doctor's orders by removing their electrodes because they are uncomfortable for mobile activities and do not allow the patient to bathe. Once removed, these electrodes are extremely difficult, if not impossible, for the patient or an untrained healthcare provider to correctly place the electrodes back on. Consequently, the monitoring suffers and the doctor cannot obtain an accurate diagnosis of the patient's medical condition. Therefore, there is a need for a method that allows for accurate placement of medical electrodes and associated harness in an ambulatory setting by a home caregiver or even the patient himself.

It is an object of the present invention to provide a method of marking a subject's skin with a permanent or semi-permanent marking, which allows for any person, untrained in the medical arts, to properly place medical electrodes onto a patient to allow for precise biopotential monitoring. This method yields many advantages to both the patient and the doctor. Hospital stays are reduced leading to lower healthcare costs. Patient quality of life is increased because there are fewer trips to and stays at the hospital and because the patient can properly replace detached electrodes after bathing or other mobile activities. More accurate monitoring is achieved through allowing the patient to remove the monitor for short periods and permitting them to replace it properly. This allows for longer-term monitoring and increases the overall accuracy of monitoring.

SUMMARY OF THE INVENTION

The present invention relates to a method for placement of certain medical devices, and in particular, to the placement of electrodes in the biopotential monitoring field. More particularly, it provides a new method for marking the skin of a subject where medical electrodes are to be placed including the placement of an electrode harness containing these electrodes.

There are numerous embodiments of the present invention, which are envisioned with a few of those listed below. The method for accurate placement of electrodes of the present invention provides a quick, efficient method of electrode placement and replacement. This method further allows homecare providers or even the patient to accurately place and replace electrodes for home health care or outpatient monitoring.

In one embodiment, the present invention includes a method of facilitating placement of electrodes comprising locating an area of a subject's outer layer of skin on which to place an electrode used for biopotential monitoring; applying ink to under the subject's outer layer of skin in the form of a tattoo; and applying the electrode to the subject's outer layer of skin in reference to the tattoo.

In another embodiment, the present invention includes a method for marking the skin of a subject in order to facilitate placement of $EKG_{[dk1]}$ electrodes comprising locating an area on a subject's outer layer of skin on which to place an EKG electrode; marking under or over the subject's outer layer of skin using a device to create a permanent or semi-permanent mark; and applying an EKG electrode on the subject's outer layer of skin in reference to the mark.

In still another embodiment, the present invention includes a method applying an electrode array to a subject comprising the steps of locating an area on a subject's outer layer of skin on which to place an electrode array comprising at least two electrodes; marking under or over the subject's outer layer of skin using a device to create a permanent or semi-permanent mark to be referenced; and applying an electrode array comprising at least one reference mark to be aligned with the permanent or semi-permanent mark under or over the subject's outer layer of skin.

Additional features and advantages of the invention will be set forth in the detailed description which follows, and in part will be readily apparent to those skilled in the art from that description or recognized by practicing the invention as described herein, including the detailed description which follows, the claims, as well as the appended drawings.

It is to be understood that both the foregoing general description and the following detailed description are merely exemplary of the invention, and are intended to provide an overview or framework for understanding the nature and character of the invention as it is claimed. The accompanying drawings are included to provide a further understanding of the invention, and are incorporated in and constitute a part of this specification. The drawings illustrate various embodiments of the invention, and together with the description serve to explain the principles and operation of the invention.

DESCRIPTION OF THE PREFERRED EMBODIMENT

Figure 1:
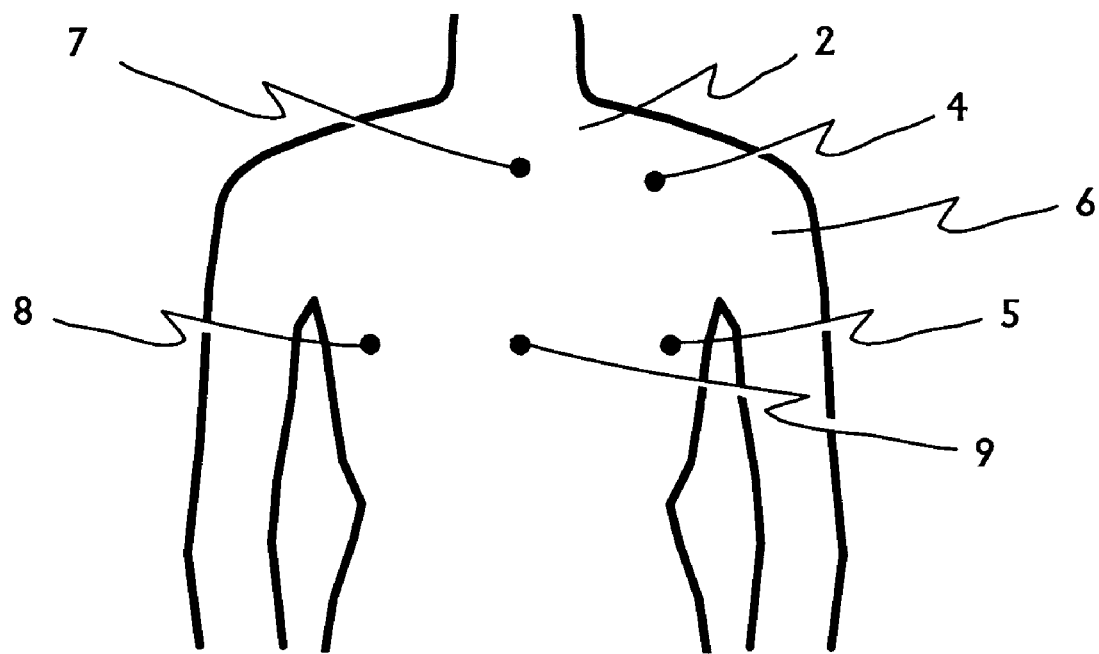
FIG. 1. is a schematic diagram showing one embodiment of the step of marking a subject under the method of the present invention.

The present invention relates to a method for placement of certain medical devices, and in particular, to the placement of electrodes in the field biopotential monitoring. More particularly, it provides a new method for marking the skin of a subject where medical electrodes are to be placed including the placement of an electrode harness containing these electrodes. These medical devices include but are not limited to ECG, EEG, EMG, electrodes and the like.

The method of the present invention comprises a number of steps and the various embodiments encompass variations of those steps. In the present invention, preferably some person locates an area on a subject on which to place an electrode, multiple electrodes, an electrode array or some combination thereof. The subject to be monitored can be any animal but preferably is a human. Generally, the area is determined by means known to those skilled in the art. Some factors affecting location selection include the end-use application or testing method which will preferably determine not only the intended anatomical location where the electrodes will be placed, but also the number and placement on the body of the subject. For example, cardiac electrophysiology protocols (ECGs) may simply require two electrodes for a low-resolution projection of cardiac electrical activity on the body surface. On the other hand, high-resolution studies may make use of more than 224 electrodes simultaneously. Each electrode placement configuration will have optimal anatomical location on the surface of the body for the most accurate readings, and the interelectrode distance will vary according to the number of electrodes used.

There are a number of different types of electrodes available today. The major types of existing electrodes include the wet surface electrodes, dry surface electrodes, invasive electrodes, and the like. The wet surface electrodes are the most commonly used electrodes today. These electrodes require a wet electrolyte gel or conductive hydrogel solution to enhance signal performance. The most commonly materials used for these electrodes include solid silver, gold, sintered silver and silver chloride, carbon, and sponge saturated with conductive gel or also called pre-gelled electrodes. The dry electrodes on the other hand do not make use of conductive gel and include non-polarizable dry electrodes (e.g. NASICON-type ceramic); active dry electrodes with built-in amplifiers, capacitively coupled electrodes coated with dielectric substances, micropenetrators or spiked based dry electrodes, etc. The invasive electrodes include the needle type electrodes designed to fully penetrate the skin of the subject to form a direct interface with bodily fluids. Preferably the wet surface electrodes and the dry surface electrodes are used in the method of the present invention.

Electrode arrays are flexible and conformable substrates which allow many individual electrodes to be placed together as a single assembly, while conforming to the shape of the anatomical geometry under the electrodes (e.g. chest, scalp, back, legs, etc). Electrode arrays are convenient devices that allow fast and accurate placement of multiple electrodes for multi-array recordings. Electrode arrays may contain built-on or preassembled electrodes, or appropriate connections for the attachment of electrodes. In addition, the electrode arrays may contain built-on circuitry and connection pads that independently connect the electrodes to a single and non-intrusive cable that connects to the signal receiver equipment. A reference point system may be included on the arrays to facilitate the identification of the appropriate anatomical regions to enhance the accurate placement of all electrodes. Overall the electrode arrays provide the opportunity for enhanced patient comfort and may reduce the risk of cross contamination as a result of minimizing or eliminating the potential for the overlapping of two or more electrodes and/or for signal interference as a result of two or more wires contacting each other. In addition it facilitates patient mobility and ambulation by minimizing or eliminating the number of cables required for connecting all electrodes to monitoring equipment.

The electrodes and/or electrode arrays used in the present invention preferably also have distinct reference points, areas or locations that are used in the placement, respectively of the electrodes and/or arrays based on markings placed on and/or anatomical features of the subject. These reference points, areas or locations could include various markings on either the electrode or electrode array, voids or cutouts, and the like. One embodiment would be to line up these reference points, areas or locations on the electrode and/or electrode array with the marking(s) and/or anatomical features on the subject.

Another step used in various embodiments of the present invention includes applying a marking under or over the subject's outer layer of skin. This marking can be any marking to those skilled in the art. The marking can include but is not limited to a tattoo both permanent and henna tattoos/semi-permanent tattoos (including but not limited to various types of tattoo inks), other types of permanent and semi-permanent inks, small marks with adhesive backing that can be placed on the subject's skin, small objects placed below the skin, a burn or branding, and the like.

Preferably, the marking is either small or can be removed so when the subject is finished with the monitoring program there is little or no visibility of the markings. One preferred embodiment of the marking is a tattoo created with inks that are of a color so that they are not very noticeable under normal lighting conditions of a subject's skin, but can be seen distinctly under another type of light such as a "black light". More preferably, these markings match or nearly match the color of the subject's skin. Another preferred embodiment of the marking is a small plastic disk with a permanent adhesive backing, which can be positioned as a marking on a subject, and can be removed with an appropriate solvent when the monitoring period is over. Still another preferred embodiment of the marking is a semi-permanent tattoo or inks that wear off after a given period of time, preferably several months. For purposes of this application, by semi-permanent it is meant that the marking will remain visible under the appropriate conditions on the subject over a reasonable period of time even after the subject washes or bathes. This reasonable period of time is preferably at least 2 days, more preferably is at least 7 days, even more preferably is at least 2 weeks, still even more preferably at least 1 month, still even more preferably is at least 3 months and most preferably is at least 6 months. Preferably, also the marking can fade or disappear, can be removed or covered in some fashion after the monitoring period is over$_{[dk2]}$.

Preferably, the marking is large enough to be seen by the person including the subject applying the electrodes but is small enough not to be highly visible to other individuals. Preferably, each marking has a surface area of between 0.001 and 2000 mm$^2$, more preferably between 0.01 and 500 mm$^2$, even more preferably between 0.25 and 100 mm$^2$, still even more preferably between 0.25 and 50 m$^{m2}$, and most preferably between 0.25 and 5 mm$^2$.

The system of marking can be used for the present invention to place individual electrodes or to place a harness with multiple electrodes. An individual marking can be used by itself or with some other anatomical feature of the subject to place the one or more electrodes or the harness containing the electrodes. One example is a marker could be used along with the sternum (or breast bone) of the subject to place an electrode harness. Multiple markings allow for an even more accurate placement of the electrode(s) or electrode harness. Preferably, at least 2 markings are used for placement of electrodes or an electrode harness, more preferably at least 4 markings are used, even more preferably at least 6 markings are used, still even more preferably at least 8 markings are used, still even more preferably at least 10 markings are used and most preferably at least 12 markings are used$_{[dk3]}$.

Another step used in various embodiments of the present invention involves applying an electrode(s) (or the electrode harness containing an electrode) to the subject's outer layer of skin in reference to the marking. This can be done by the subject, a friend, a family member, a home healthcare provider or a medical professional. The markings, however, make it simpler for an unskilled individual to accurately apply the monitoring electrode(s) or electrode harness. The markings also make it quicker for a healthcare provider or medical professional to make the application.

Figure 2:
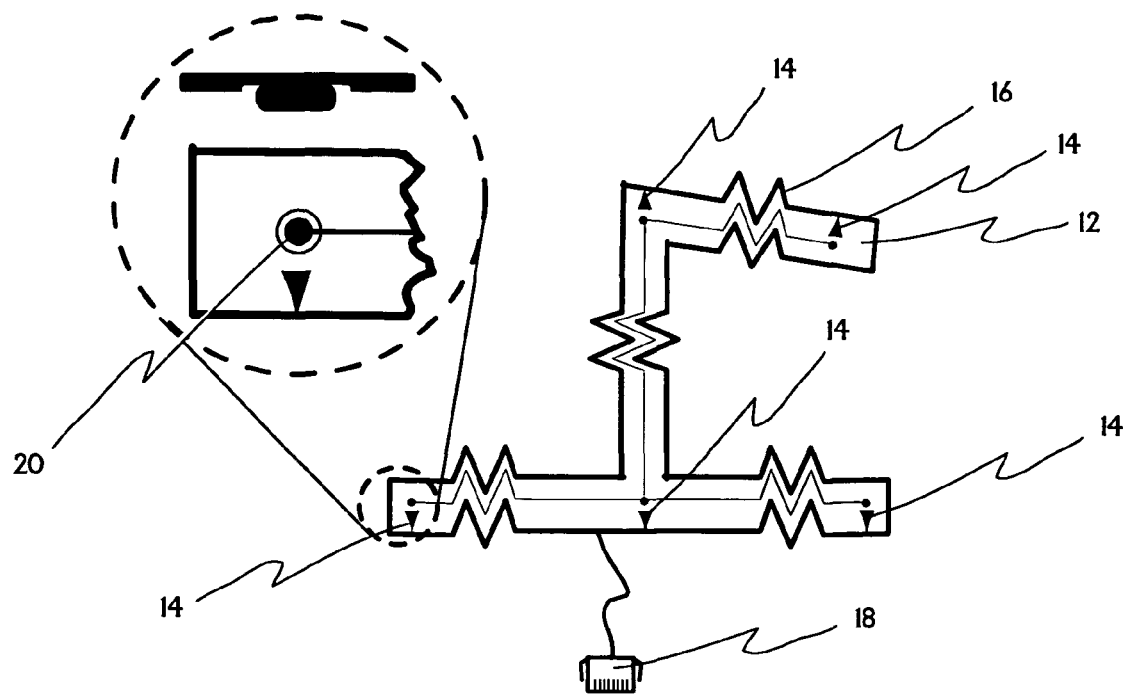
FIG. 2. is a schematic diagram showing an electrode array with reference marks for alignment on the subject shown in FIG. 1.
Figure 3:
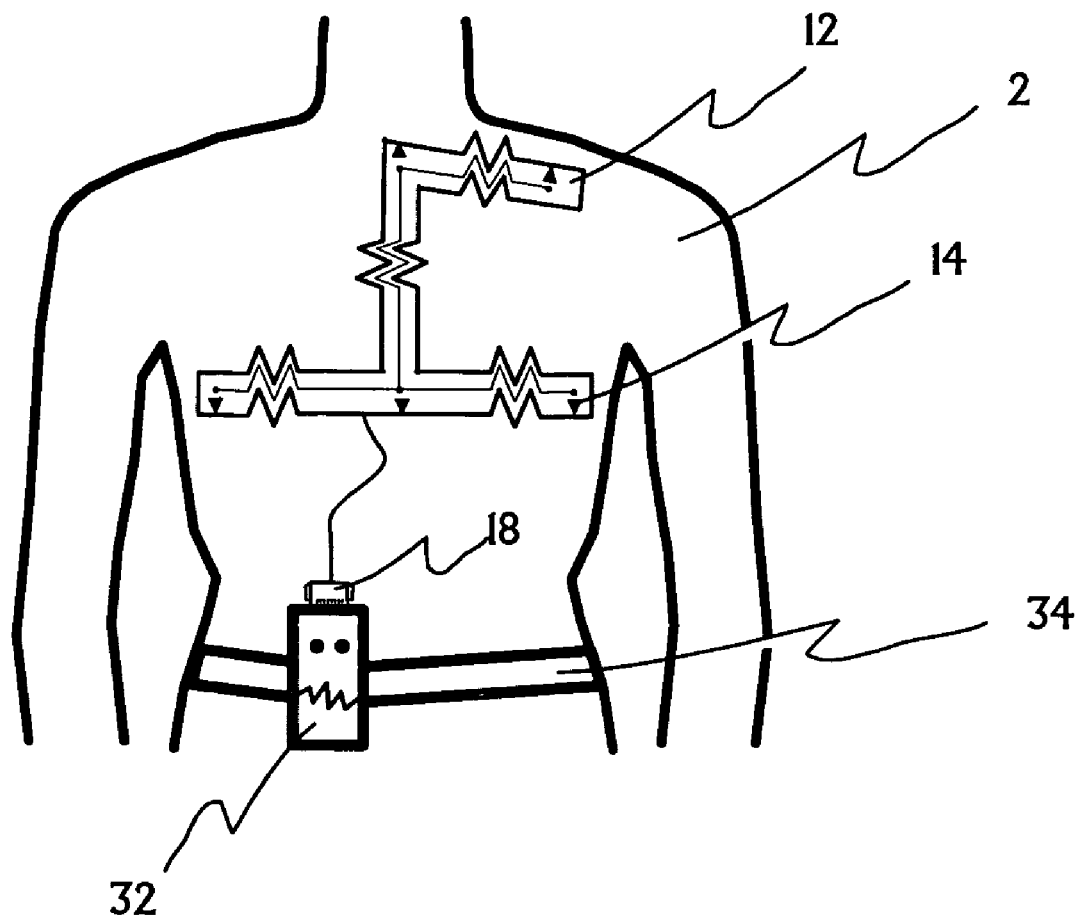
FIG. 3. is a schematic diagram showing the electrode array in FIG. 2 aligned to the markings on the subject shown in FIG. 1.

FIGS. 1-3 demonstrate the use of this marking system on a human subject. FIG. 1 is a schematic diagram showing one embodiment of the step of marking a subject under the method of the present invention. In FIG. 1 the subject 2 is marked under or over the subject's outer layer of skin 6 using a device to create a permanent or semi-permanent mark. In this particular embodiment, the subject 2 actually has five marks 4, 5, 7, 8 and 9, which are placed on the subject's thorax. FIG. 2 is a schematic diagram showing an electrode array 12 with reference marks for alignment on the subject 2 shown in FIG. 1. In the particular embodiment of the electrode array 12 in FIG. 2, the electrode array 12 contains five reference marks 14 to be aligned with the permanent or semi-permanent marks 4, 5, 7, 8 and 9 shown in FIG. 1 under or over the subject's 2 outer layer of skin 6. The electrode array 12, in this embodiment, further includes a connector 18 for connecting the electrode array to a processing or monitoring device (not shown), and flexible arms 16 to allow for positioning of the array 12. The call-out 20 shows both a planar and a side view of one of the electrodes and corresponding reference mark of the electrode array 12.

FIG. 3 is a schematic diagram showing the electrode array 12 in FIG. 2 aligned to the markings 4, 5, 7, 8, and 9 on the subject 2 shown in FIG. 1. It will be noted that the electrode array in FIG. 3 is aligned to the markings by being placed so as to cover (or be aligned over), to overlap or to touch the markings. In addition, in this embodiment the connector 18 for the electrode array 12 connects the electrode array 12 with a wireless monitoring and/or transmission device 32 for relaying the biopotential signal picked up from the subject 2.

It will be apparent to those skilled in the art that various modifications and variations can be made to the present invention without departing from the spirit and scope of the invention. Thus, it is intended that the present invention cover the modifications and variations of this invention provided they come within the scope of the appended claims and their equivalents.

What is claimed is:

1. A method of facilitating placement of electrodes for biopotential monitoring comprising the steps of
   a. locating an area of a human subject's outer layer of skin on which to place an electrode used for biopotential monitoring;
   b. applying ink to under the subject's outer layer of skin in the form of a tattoo; and
   c. applying the electrode to the subject's outer layer of skin by placing the electrode so the electrode is touching or over the tattoo.

2. The method in claim 1, wherein ink is applied in at least two locations creating at least two distinct tattoos and wherein at least two electrodes are applied to a subject's outer layer of skin by placing the at least two electrodes so they touch or are over the at least two distinct tattoos.

3. The method in claim 1 wherein the tattoo has a surface area of between 0.01 mm$^2$ and 100 mm$^2$.

4. The method in claim 1, wherein the electrode which is applied to the subject's outer layer of skin is part of an electrode array.

5. The method in claim 2, wherein the at least two electrodes are part of an electrode array.

6. The method in claim 1, wherein the ink is not highly visible using visible light.

7. The method in claim 5, wherein the ink is not highly visible using visible light.

8. A method for marking the skin of a subject in order to facilitate placement of an EKG electrode array with at least two electrodes, the method comprising:
   a. locating an area on an outer layer of skin of a subject's thorax on which to place an EKG electrode array with at least two electrodes;
   b. marking the subject's thorax using a device to create a mark that is a tattoo applied under thorax; and
   c. applying an EKG electrode array comprising at least two electrodes to the outer layer of skin of the subject's thorax after marking under the outer layer of skin of the subject's thorax with a tattoo, the EKG electrode array with at least two electrodes comprising at least one distinct reference mark, void or cutout on the electrode array to touch or be placed over the tattoo applied under the outer layer of skin of the subject's thorax.

9. The method in claim 8, wherein at least two distinct marks that are tattoos are made under the outer layer of skin of the subject's thorax.

10. The method in claim 9, wherein an EKG electrode array with at least two electrodes is applied to the outer layer of skin of the subject's thorax in reference to the at least two distinct marks that are tattoos made under the outer layer of skin of the subject's thorax.

11. The method in claim 8, wherein the mark is a tattoo that is made from a biodegradable marking material.

12. The method in claim 8, wherein the at least two electrodes of the EKG electrode array are dry surface electrodes.

13. The method in claim 8, wherein the mark is a tattoo that is not highly visible using visible light.

14. The method in claim 11, wherein the biodegradable marking material remains visible for a period of at least 2 weeks.

15. A method of applying an electrode array for biopotential monitoring to a human subject comprising the steps of;
   a. locating an area on a human subject's outer layer of skin on which to place an electrode array for biopotential monitoring comprising at least two electrodes;
   b. marking under the subject's outer layer of skin using a device to create a mark to be referenced, the mark being a tattoo; and
   c. applying an electrode array for biopotential monitoring to the subject's outer layer of skin, the electrode array comprising at least one reference mark, void or cutout to touch or be placed over the mark made under the subject's outer layer of skin.

16. The method in claim 15, wherein at least two distinct marks that are tattoos are made under the subject's outer layer of skin.

17. The method of claim 15, wherein the electrode array for biopotential monitoring is an electrode array for monitoring EEG signals.

18. The method of claim 15, wherein the mark is a tattoo that is not highly visible using visible light.

19. The method of claim 17, wherein the electrode array for monitoring EEG signals comprises at least one dry surface electrode.

20. The method of claim 15, wherein the mark is a tattoo that is made from a biodegradable marking material.

* * * * *